US00PP09962P

United States Patent [19]

Bradford et al.

[11] Patent Number: Plant 9,962

[45] Date of Patent: Jul. 15, 1997

[54] NECTARINE TREE 'SPRING SWEET'

[76] Inventors: Lowell Glen Bradford, 12439 E. Savana Rd.; Norman G. Bradford, 11875 E. Savana Rd., both of Le Grand, Calif. 95333

[21] Appl. No.: 654,082

[22] Filed: May 28, 1996

[51] Int. Cl.[6] ..... A01H 5/00

[52] U.S. Cl. ..... Plt./41.1

[58] Field of Search ..... Plt./41.1

[56] References Cited

U.S. PATENT DOCUMENTS

P.P. 8,923 10/1994 Bradford et al. ..... Plt./41.3

P.P. 9,360 11/1995 Bradford et al. ..... Plt./40.1

*Primary Examiner*—James R. Feyrer

[57] ABSTRACT

The present invention relates to a nectarine *Prunus persica* tree and more particularly to a new and distinct variety broadly characterized by a large size, vigorous, hardy, productive and regular bearing tree. The fruit matures under the ecological conditions described approximately the third week in June, with first picking on Jun. 21, 1995. The fruit is uniformly medium in size, excellent in flavor, attractively globose in shape, clingstone in type, very firm in texture, and full red in skin color. The variety was developed as a first generation hybridization using Kay Diamond Nectarine (U.S. Plant Pat. No. 8,923) as the selected seed parent and June Pearl Nectarine (U.S. Plant Pat. No. 9,360) as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Spring Sweet". The present variety was hybridized in 1992 by us in a cultivated area of our experimental orchard at Bradford Farms near Le Grand, Calif. in Merced County (San Joaquin Valley). It was the result of a first generation hybridization using Kay Diamond (U.S. Plant Pat. No. 8,923) yellow flesh nectarine as the selected seed parent and June Pearl (U.S. Plant Pat. No. 9,360) white flesh nectarine as the selected pollen parent. Subsequent to origination of the present variety of nectarine tree, we asexually reproduced it by budding and grafting, and such reproduction of plant and fruit characteristics were true to the original plant in all respects.

The present variety is most similar to its seed parent, the Kay Diamond (U.S. Plant Pat. No. 8,923) nectarine by producing fruit that is yellow in flesh color, very firm in texture, clingstone in type, and full red in skin color, but is distinguished therefrom and an improvement thereon by producing fruit that is clingstone instead of freestone, that is subacidic in flavor instead of acidic, that has a bitter kernel instead of sweet, and that matures about 5 days later.

The present variety is similar to its pollen parent, the June Pearl (U.S. Plant Pat. No. 9,360) white flesh nectarine, by producing full red colored clingstone nectarines that are subacidic in flavor, but is very distinguished therefrom by producing fruit that is yellow in flesh color instead of white, that ripens approximately 10 days later, and that is not prone to protruding apexes.

DRAWING

The accompanying photograph exhibits four whole fruits positioned to display the characteristics of the skin color and form, a sectioned half fruit divided transverse to the suture plane to reveal the flesh and stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jun. 23, 1995. All major color code designations are by reference to the Inter-Society Color Council, National Bureau of Standards. Common color names are also used occasionally.

TREE

Size: Large. Vigor: Vigorous. Growth: Spreading and dense. Form: Vase formed. Hardiness: Hardy. Production: Productive. Bearing: Regular bearer. Trunk:

- *Size.*—Medium.
- *Texture.*—Medium.
- *Bark color.*—Dark grayish yellowish brown [81. d.gy.yBr].
- *Lenticles.*—Numerous. Color: Dark brown [59. d.Br]. Average size: 3/16" [4.8 mm.].

Branches:

- *Size.*—Medium.
- *Texture.*—Medium.
- *Color.*—1st year wood topside: Moderate purplish red [258. m.pR]. 1st year wood underside: Light yellow green [119. 1YG]. Older wood: Moderate brown [58. m.Br].
- *Lenticels.*—Numerous, very small. Color: Dark yellowish brown [78. d.yBr]. Average Size: 1/16" to 1/8" [1.6–3.2 mm.].

Leaves:

- *Size.*—Medium. Average length: 5½" [139.7 mm.]. Average width: 1 9/16" [39.7 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125. m.OlG]. Ventral surface: Moderate yellow green [120. m.YG].

*Margin.*—Finely serrate.
*Venation.*—Pinnately net veined.
*Petiole.*—Average length: ½" [12.7 mm.]. Average thickness: 1/16" [1.6 mm.]. Color moderate yellow green [120. m.YG].
*Stipules.*—Numerous. Average length: ⅜" [9.5 mm.].
*Glands.*—Average number: 2–4 per leaf. Position: Alternately positioned on petiole and base of blade. Size: Medium. Form: Reniform. Color: Brilliant yellow green [116. brill.YG].

Flower buds:
Hardness.—Hardy.
Size.—Medium.
Length.—Medium.
Form.—Free.
Surface.—Pubescent.

Flowers:
Blooming period.—Medium as compared with other varieties.
Size.—Large.
Color.—Pale purplish pink [252. p.pPk].

FRUIT

Maturity when described: Firm eating ripe, Jun. 23, 1995.
Date of first picking: Jun. 21, 1995.
Date of last picking: Jun. 28, 1995.
Size: Uniform, medium.
*Average diameter axially.*—2⅝" [66.7 mm.].
*Average transversely in suture plane.*—2½" [63.5 mm.].
Form: Uniform, globose, slightly asymmetrical, slightly truncate at the base.
*Longitudinal section form.*—Circular.
*Transverse section through diameter.*—Circular.
Suture: A shallow groove extending from the base to beyond the apex, having a slight depression beyond the pistil point.
Ventral surface: Rounded, lipped throughout, but stronger on one side.
Lips: Somewhat unequal.
Cavity: Flaring, somewhat elongated in the suture plane, suture showing on one side, stem markings typical.
*Depth.*—7/16" [11.1 mm.].
*Breadth.*—⅝" [15.9 mm.].
Base: Rounded to somewhat truncate.
Apex: Rounded.
Pistil point: Apical, with most depressed within the suture.
Stem: Medium.
*Average length.*—⅜" [9.5 mm.].
*Average width.*—3/16" [4.8 mm.].

Skin:
*Thickness.*—Medium.
*Texture.*—Medium.
*Tenacity.*—Tenacious to flesh.
*Tendency to crack.*—Slight in the wet season.
*Color.*—Very deep red [14. v.deep R] over a dark reddish orange [38. d.rO] background with some strong orange yellow [68. s.OY] freckling toward the apex.

Flesh:
*Color.*—Brilliant yellow [83. brill.Y] to the pit, with virtually no red at the stone.
*Amygdalin.*—Scarce.
*Juice.*—Abundant, rich.
*Texture.*—Firm, crisp.
*Fibers.*—*Abundant, fine.*
*Ripens.*—Evenly.
*Flavor.*—Subacidic and sweet with 15 brix.
*Aroma.*—Moderate.
*Eating quality.*—Very good.

STONE

Type: Clingstone.
Form: Oval.
Base: Straight.
Apex: Acute to acuminate.
Sides: Equal.
Surface: Pitted toward the base, irregularly furrowed near the apex.
Ridges: Jagged toward the base.
Color: Moderate orange [53. m.O] when first removed, light brown [57. l.Br] internally.
Pit wall: ¼" [6.4 mm.] thick.
Tendency to split: None observed.
Kernel:
*Form.*—Oval.
*Taste.*—Bitter.
*Viable.*—Yes.
*Average width.*—½" [12.7 mm.].
*Average length.*—¾" [19.1 mm.].
*Color.*—Pale yellow [89. p.Y] when first removed.
*Pellicle color.*—Brownish orange [54. brO].
*Amygdalin.*—Abundant.

USE

Market: Fresh and long distance shipping.
Keeping quality: Good.
Shipping quality: Good.
Resistance to insects: No unusual susceptibilities noted.
Resistance to Diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to its seed parent, the Kay Diamond (U.S. Plant Pat. No. 8,923) nectarine by producing fruit that is yellow in flesh color, very firm in texture, and full red in skin color, but is distinguished therefrom and an improvement thereon by producing fruit that is clingstone instead of freestone, that is subacidic in flavor instead of acidic, that has a bitter kernel instead of sweet, and that matures about 5 days later.

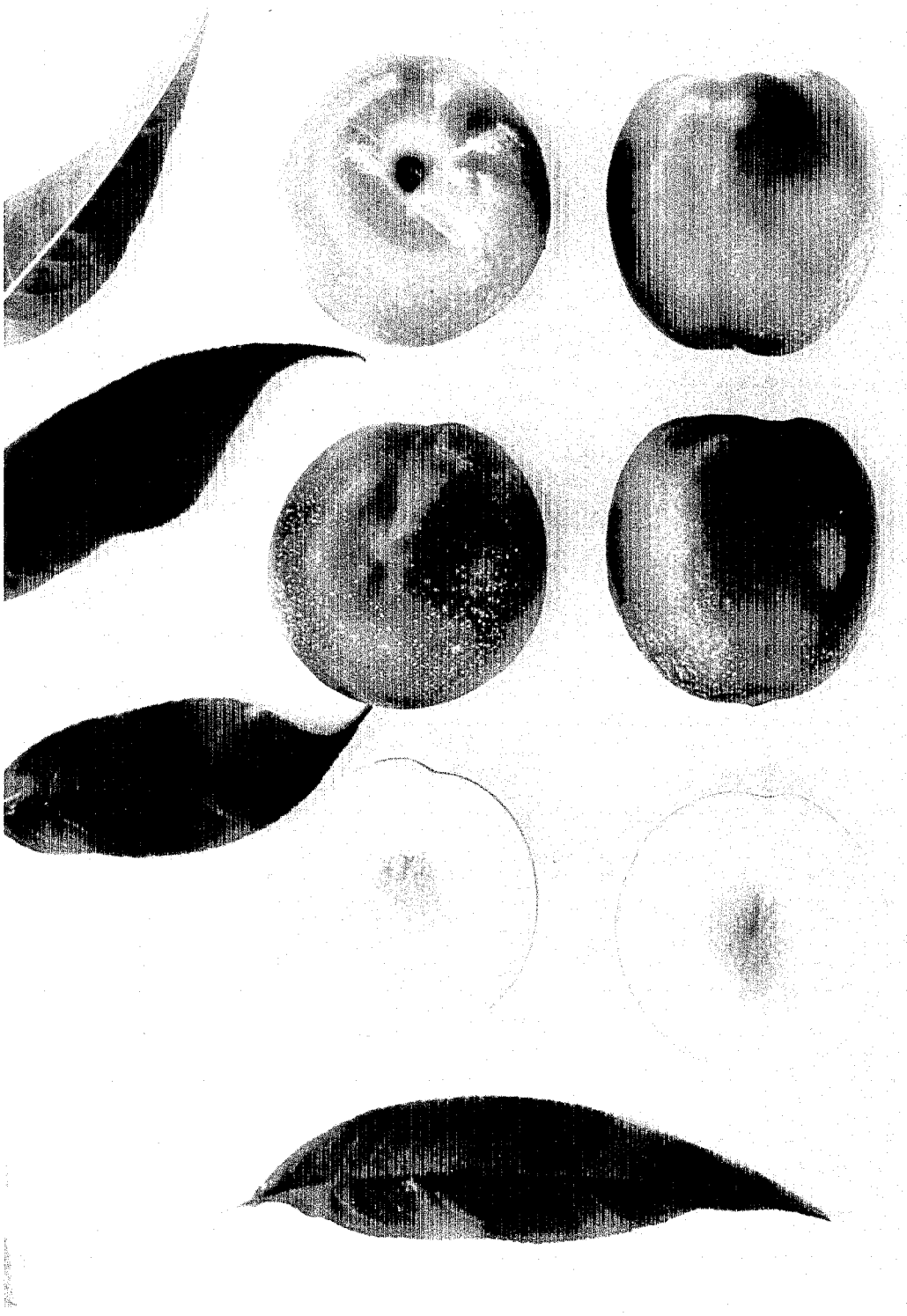

* * * * *